(12) United States Patent
Wang et al.

(10) Patent No.: US 8,716,399 B2
(45) Date of Patent: May 6, 2014

(54) POLYSACCHARIDE-GRAFTED POLYETHYLENIMINE AS A GENE CARRIER

(75) Inventors: Li-Fang Wang, Koahsiung (TW);
Kuo-Hsun Sung, Kaohsiung (TW);
Yu-Lun Lo, Nantou County (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 13/299,826

(22) Filed: Nov. 18, 2011

(65) Prior Publication Data

US 2013/0030119 A1 Jan. 31, 2013

(30) Foreign Application Priority Data

Jul. 25, 2011 (TW) ............... 100126252 A

(51) Int. Cl.
*A61K 47/48* (2006.01)
(52) U.S. Cl.
USPC ...................................... 525/54.2; 525/54.21
(58) Field of Classification Search
USPC ............................................. 525/54.2, 54.21
See application file for complete search history.

(56) References Cited

U.S. PATENT DOCUMENTS 6,018,033 A 1/2000 Chen et al.

FOREIGN PATENT DOCUMENTS

| TW | 201018523 | | 5/2010 | |
| WO | 2010/083039 | | 7/2010 | |
| WO | WO 2010/083039 | * | 7/2010 | ............ C08F 251/00 |

OTHER PUBLICATIONS

Lu, B., et al; Biomacromolecules, 2008, p. 2594-2600.*
Pathak, A., et al.; ACS Nano, 2009, p. 1493-1505.*
U.S. Appl. No. 13/074,491, filed Mar. 29, 2011.
Lu, B et al., "Low molecular weight polyethylenimine grafted N-maleated chitasan for gene delivery: properties and in vitro transefction studies," 2009, Biomacromolecules, 9: 2594-2600.
Pathak, A et al., "Gene expression, biodistribution, and pharmacoscintigraphic evaluation of chondroitin sulfate-PEI nanoconstructs mediated gene therapy," 2009, ASC Nana, 3(6):1493-1505.
Taiwanese Office Action in Taiwanese Application 10012652 dated Sep. 9, 2013.
Non-Final Office Action for U.S. Appl. No. 13/782,312, filed Mar. 1, 2013, dated Feb. 13, 2014, 11 pages.

* cited by examiner

*Primary Examiner* — Robert Jones, Jr.
(74) *Attorney, Agent, or Firm* — Volpe and Koenig, P.C.

(57) ABSTRACT

The present invention discloses a gene carrier and the preparation method thereof. Chondroitin sulfate (CS) is reacted with methacrylic anhydride (MA) to form chrondroitin sulfate-methacrylate (CSMA), which is further covalently bound with polyethylenimine (PEI) via the Michael addition to produce a CSMA-PEI gene carrier. The CSMA-PEI gene carrier can effectively reduce the cytotoxicity of PEI and enhance the transfection efficiency of PEI.

14 Claims, 7 Drawing Sheets

US 8,716,399 B2

POLYSACCHARIDE-GRAFTED POLYETHYLENIMINE AS A GENE CARRIER

CROSS-REFERENCE TO RELATED APPLICATION AND CLAIM OF PRIORITY

The application claims the benefit of Taiwan Patent Application No. 100126252, filed on Jul. 25, 2011, in the Taiwan Intellectual Property Office, the disclosures of which are incorporated herein in their entirety by reference.

FIELD OF THE INVENTION

The present invention relates to a gene carrier. In particular, the present invention relates to a polysaccharide-grafted polyethylenimine as a gene carrier.

BACKGROUND OF THE INVENTION

Polyethylenimine (PEI) is one of the most potent gene carriers, and the high transfection efficiency of PEI has been postulated to relate to its buffering capacity, which leads to the accumulation of protons bought in by endosomal ATPase and an influx of chloride anions, triggering endosome swelling and disruption, followed by the release of gene drugs such as DNA or siRNA into cytoplasm.

The inventors of the present invention discloses a PAAIO-PEI nanoparticle prepared by using PEI and $Fe_3O_4$ as the materials in U.S. patent application Ser. No. 13/074,491 filed on Mar. 29, 2011. The PAAIO-PEI nanoparticle can be a non-viral gene carrier for carrying genetic material, is able to sustain superparamagnetic property, has less cytotoxicity than PEI, and shows better transgene expression efficiency than PEI under the disturbance of fetal bovine serum.

Additionally, Taiwan patent publication No. 201018523 discloses a liposome. For avoiding the activity attenuation of liposome-binding protein which is caused by chemical modification on liposome and reducing the purification steps of the chemically modified liposome, in that patent application, the positive charged polymers (e.g. PEI) and the surfactant polymers are distributed on the neutral lipid membrane with hollow spherical structure via non-covalently bonded combination, to form liposome. However, the patent publication does not overcome the cytotoxicity generated by PEI.

Although PEI has the above advantages and the applications in the prior art, for overcoming PEI's toxicity and owning it high capacity of passing through cellular membrane, the solution to PEI's high toxicity is still a problem necessary to be solved in the clinic application.

It is therefore attempted by the applicant to deal with the above situation encountered in the prior art.

SUMMARY OF THE INVENTION

The natural negative charged polysaccharide, i.e. chrondroitin sulfate (CS), is adopted as the material in the present invention, and CS is modified with covalent bonding, so that the double bond-modified CS is reacted with PEI via Michael addition to form the covalent bond in between, and a low toxicity and high water-soluble gene carrier is formed. In addition, the high capability nano-leveled gene carrier can be obtained by adjusting the ratio between CS and PEI to control the positive charge-negative charge ratio. The CS-modified PEI may differ a cellular internalization mechanism from PEI, resulting in the reduced cytotoxicity, but retains the gene transfecting efficiency as PEI does.

The present invention provides a preparation method of a gene carrier, including steps of: reacting CS with methacrylic anhydride (MA) to form chrondroitin sulfate-methacrylate (CSMA); and covalently bonding PEI with CSMA to form the gene carrier.

After CSMA is generated, CSMA is precipitated with ethanol. Before PEI and CSMA is covalently bonded, PEI is mixed with pyridine. After the gene carrier is prepared, the gene carrier is dialyzed to remove the redundant PEI using the dialysis membrane. In addition, the gene carrier is capable of carrying the genetic material such as DNA, RNA, complementary DNA (cDNA), micro RNA, small interfering RNA and so on.

The present invention further provides a gene carrier prepared based on the above preparation method, the gene carrier includes CS, methacrylate bonded with CS, and PEI, wherein MA is covalently bonded with CS to form CSMA, and then PEI is covalently bonded with the methacrylate group of the CSMA.

Preferably, the prepared gene carrier is capable of carrying the genetic material described.

The present invention further provides a gene carrier, including: a saccharide (or carbohydrate) having a double-bond group; and a positive charge molecule having an amino group covalently bonded with the double-bond group.

The saccharide includes polysaccharides such as CS, chitosan, chitin, hyaluronic acid, dextran, and heparin. The double-bond group is originated from acrylate or methacrylate and is a carbon-carbon double-bond group such as acryloyl chloride, acrylic anhydride, methacryloyl chloride, and methacrylic anhydride. The positive charge molecule includes PEI and polylysine.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

Figure 1A:
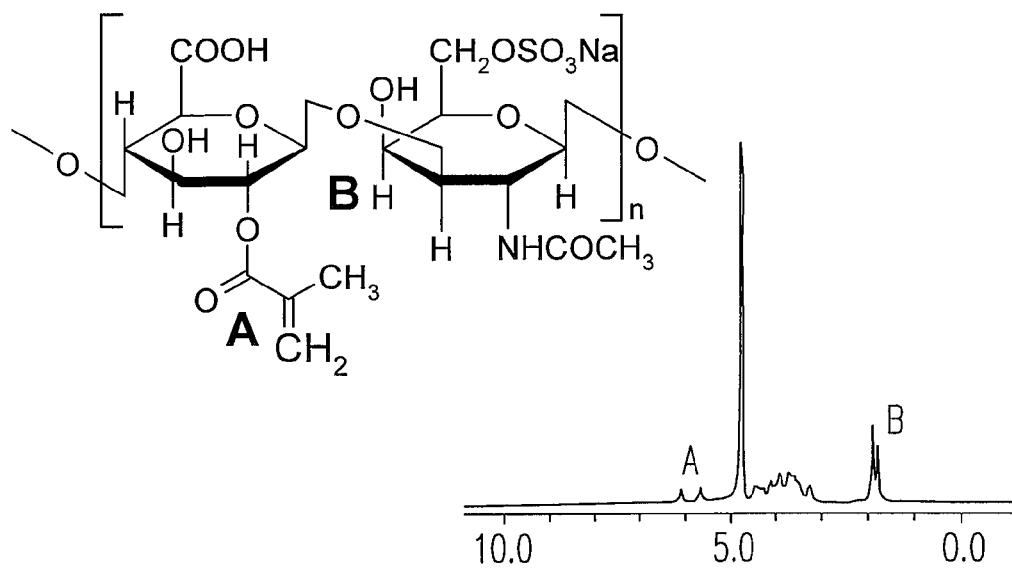
FIG. 1(a) to FIG. 1(c) respectively depict the $^1$H-NMR spectra of (a) double bond-modified CSMA, (b) PEI and (c) CSMA-PEI.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

The gene carrier sought protected in the invention includes two parts, one is macromolecule such as hydrocarbon molecule (e.g. saccharide, polysaccharide and others), and the other is positive charge molecule. The amino group of the positive charge molecule forms a covalent bonding with the double-bonded group of hydrocarbon. The generated "hydrocarbon-positive charge molecule" is able to be the gene carrier, and further transfects genetic material such as DNA, RNA, complementary DNA (cDNA), microRNA, small interference RNA (siRNA) and so on into cells or tissues, so that the therapeutic or cytotoxic effect is achieved. Additionally, the examples of double-bond group are originated from molecules such as acrylate ($CH_2=CHCOO^-$), methacrylate ($CH_2=CMeCOO^-$) and others. In particular, the double-bond groups is a carbon-carbon double bond group originated from molecules such as acryloyl chloride, acrylic anhydride, methacryloyl chloride, methacrylic anhydride and so on. The examples of positive charge molecule are polyethylenimine (PEI), polylysine (or poly-L-lysine) and so on.

In one embodiment of the invention, chondroitin sulfate (CS) was modified with methacrylic anhydride (MA) to form chondroitin sulfate-methacrylate (CSMA), and then the positive charge polyethylenimine (PEI) formed covalent bond with CSMA to afford chondroitin sulfate-methacrylate-polyethylenimine (CSMA-PEI) gene carrier. This CSMA-PEI gene carrier was a positive charge water-soluble polymer, and a polyelectrolyte was formed to carry genetic material by using the electrostatic attraction force formed between the amino group and the genetic material, and the genetic material was delivered to cells or tissues via an endocytosis mechanism. The reaction formulas I and II of the embodiment of the invention were illustrated as follows.

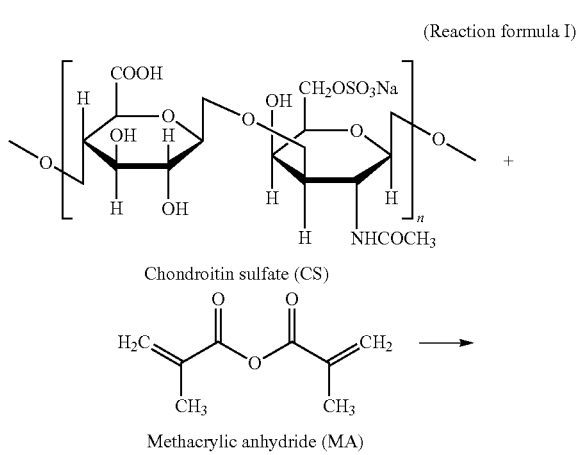

In addition to CS, other polysaccharides such as chitosan, chitin, dextran, heparin, and hyaluronic acid also can be the candidates as the materials for preparing the gene carrier.

I. Preparation of Chondroitin Sulfate-Methacrylate (CSMA):

Chondroitin sulfate (CS, 5 g) was dissolved in dd$H_2O$ (250 mL), methacrylic anhydride (MA, 60 mL) was added dropwise into the CS solution, and then 5N sodium hydroxide (NaOH) solution was added dropwise to react for 48 hours. Next, the reaction mixture was disposed at 4° C. overnight to cease the reaction. The reaction mixture was repeatedly precipitated with abundant ethanol and centrifuged (at 6,000 rpm for 5 minutes), and the precipitation was dried for 48 hours in the vacuum oven to obtain CSMA.

II. Preparation of CSMA-Polyethylenimine (CSMA-PEI):

CSMA-PEI with different amounts of PEI could be prepared in accordance with the technology in the invention. CSMA-PEI with high, middle, or low amount of PEI defined as CP(H), CP(M), and CP(L) in the invention was illustrated as follows, and CSMA-PEI with other amount of PEI could be prepared in accordance with the similar method by the skilled person in this art.

PEI (1.5 g, molecular weight was about 10K Dalton) was dissolved in ddH$_2$O (1.5 L). After PEI was completely dissolved, pyridine (1.5 mL) was added and stirred for 2 hours. The CSMA solution (52.7 mg CSMA dissolved in 52.7 mL ddH$_2$O) was added dropwise into the aforementioned PEI solution and reacted in ambient temperature for 48 hours. The redundant PEI was removed using dialysis membrane (the allowable molecular weight to dialysis was about 25000 Dalton), the CSMA-PEI solution was lyophilized to obtain CSMA-PEI with high amount of PEI. CSMA-PEI with middle or low amount of PEI was prepared using the same preparation method and the PEI starting material (m.w. about 10K Dalton) of 300 mg and 100 mg, respectively.

III. Preparation and Properties of CSMA-PEI/pDNA Nanoparticles:

The preparation of CSMA-PEI gene carrier for carrying genetic materials was made by controlling the concentration of CSMA-PEI gene carrier to adjust the ratio of CSMA-PEI gene carrier to genetic material (such as plasmid DNA (pDNA)) in terms of N/P ratio. CSMA-PEI gene carrier and plasmid DNA solution with the same volumes were mixed at a ratio of 1 to 9 and then vortexed immediately. CSMA-PEI/pDNA nanoparticles were disposed at ambient temperature for 30 minutes to perform complete complex before analysis. N/P value can be an integral number such as 1, 2 to 9 or a non-integral number from 1 to 9, such as 1.5, 2.5 and so on. The used plasmid DNA in the experiments of the invention includes but not limit in the commercial pEGFP-C1 (Clontech), pGL3 (Promega), other commercial plasmids or self-designed and prepared plasmids.

The conjugation ability of CSMA-PEI gene carrier to the genetic material could be evaluated by agarose gel electrophoresis. The CSMA-PEI/pDNA nanoparticles prepared based on the aforementioned method and different N/P ratios were used to determine the stability of nanoparticles using 0.8% agarose gel electrophoresis after mixing for different time periods in presence or absence of 10% fetal bovine serum (FBS).

Dynamic Light Scattering (DLS) and Zeta Potential

The averaged hydrodynamic diameter and zeta potential of CSMA-PEI/pDNA were measured by laser Doppler anemometry using a Zetasizer Nano ZS instrument (Marlvern, Worcestershire, UK). Light scattering measurements were carried out with a laser at 633 nm with a 90° scattering angle. The concentration of the sample was 0.1 mg/mL and the temperature was maintained at 25° C. Polystyrene nanospheres (220±6 nm and −50 mV; Duke Scientific, USA) were used to verify the performance of the instrument. The particle size and zeta potential of each sample were performed in triplicate.

Transmission Electron Microscopy (TEM)

The size and morphology of magnetoplexes were visualized by cryo-TEM (Jeol JEM-1200, Tokyo, Japan). A carbon coated 200 mesh copper specimen grid (Agar Scientific Ltd. Essex, UK) was glow-discharged for 1.5 minutes. One drop of the sample solution was deposited on the grid and left to air-dry at room temperature, and was then examined with an electron microscope.

IV. Cytotoxicity Assay:

U87 cells (human glioblastoma cell line) were seeded in 12-well tissue culture plates at a density of 1×10$^5$ cells per well in MEM (Minimum essential medium) containing 10% FBS for 24 hours. Cytotoxicity of CSMA-PEI nanoparticles was evaluated by determining the cell viability after 4 hours incubation of cells with CSMA-PEI gene carrier (or CSMA-PEI/pDNA nanoparticles) in a serum-free MEM followed by 72 hours post incubation in the MEM containing 10% FBS at the same condition. The number of viable cells and viability were determined by estimation of their mitochondrial reductase activity using the tetrazolium-based colorimetric method (MTT conversion test) known by the skilled person in this art.

V. Transfection Efficiency:

U87 cells were seeded at a density of 1×10$^5$/well in 12 well plates and incubated in MEM (Minimum essential medium) containing 10% FBS for 24 hours before transfection. When the cells were at 50% to 70% confluence, the culture medium was replaced with 1 mL of MEM with or without 10% FBS. In addition, pEGFP-C1 (control, 4 µg) and CSMA-PEI/pEGFP-C1 nanoparticles (4 µg) were prepared, and the medium was replaced with fresh complete-medium and the cells were incubated for 48 hours post transfection after pEGFP-C1 or CSMA-PEI/pEGFP-C1 nanoparticles were cultured with cells for 6 hour incubation. The green fluorescent protein (GFP) expression was directly visualized under a fluorescence microscope.

For the luciferase assay, the procedures as stated above were made to determine the transfection efficiency of the CSMA-PEI/pGL3 nanoparticles compared with naked pGL3 plasmid DNA (as a negative control), Lipofectamine (a positive control), and PEI/pGL3 polyplex at a weight ratio of 10 (a positive control) in U87 cells. To quantify the luciferase expression, transfected cells were rinsed gently with 1 mL of 0.1 M PBS (phosphate buffered saline, twice), and then added to 200 µL/well of lysis buffer (0.1 M Tris-HCl, 2 mM ethylenediaminetetraacetic acid (EDTA), and 0.1% Triton X-100, pH 7.8) and let stand overnight at −20° C. Next day, each cell lysate was warmed to room temperature and centrifuged at high speed for 30 minutes. The luciferase activity was monitored using the TopCount NXT™ microplate scintillation and luminescence counter (Perkin Elmer, N.J., USA) after mixing the supernatant with the luciferase assay reagent (Promega, Madison, Wis., USA). The total protein content of the cell lysate was examined using a BCA protein assay kit (Pierce Rockford, Ill., USA).

VI. Characteristics of CSMA-PEI Gene Carrier:

Since PEI was known to has high transfection ability and was the most widely used non-viral carrier in clinics, its cytotoxicity was still high. Therefore, in the invention, PEI was bound to the double-bonded CSMA based on the transfection ability of PEI and covalent bonding, and the stable and positive charge CSMA-PEI gene carrier was formed by regulating the ratio of CSMA to PEI.

Figure 1B:
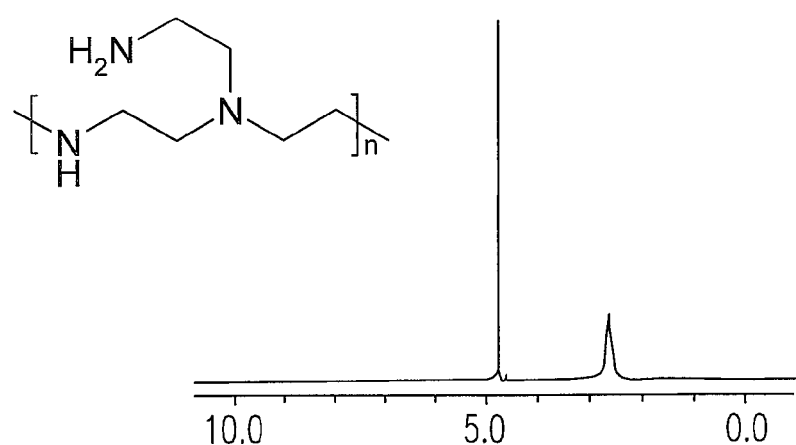
Figure 1C:
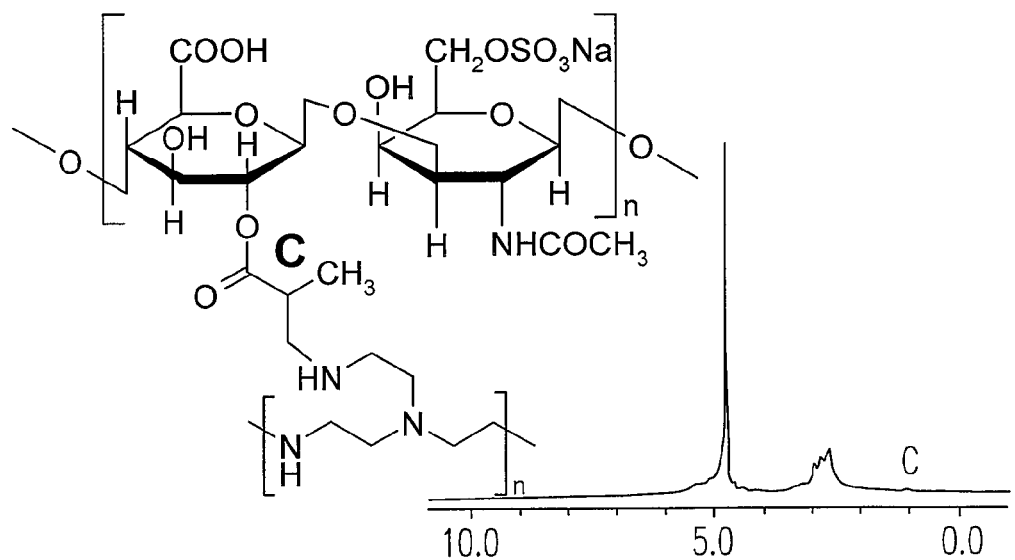

Please refer to FIGS. 1(a) to 1(c), respectively depict the $^1$H-NMR spectra of (a) CSMA, (b) PEI and (c) CSMA-PEI. It could be known that Michael addition was performed between CSMA and PEI. The double-bond portion (i.e. the denotation "A", d=5.6 ppm, 6.1 ppm) of CSMA in FIG. 1(a) was reacted with the amino group (d=2.6 ppm) of PEI in FIG. 1(b) to form carbon-nitrogen single bond, and $^1$H-NMR spectrum of CSMA-PEI (i.e. the denotation "C" in FIG. 1(c)) showed the signal at d=1.1 ppm. Additionally, the denotation "B" in FIG. 1(b) was referred to CSMA. Furthermore, it was proved from DLS experiment that no particle was reproduced in hydrous solution (not shown), and thus CSMA and PEI formed the CSMA-PEI gene carrier by the covalent bond rather than attraction force of charge.

Figure 2:
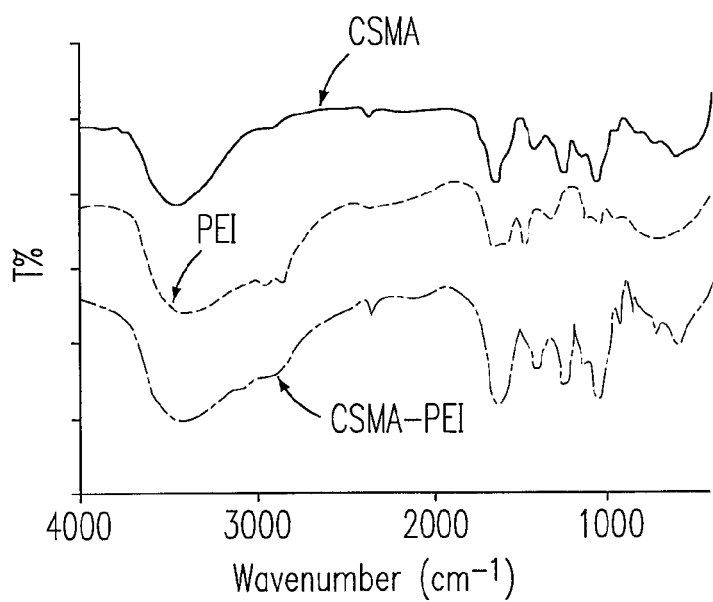
FIG. 2 depicts the Fourier transform analysis spectra of CSMA, PEI and CSMA-PEI.

In quality, please refer to FIG. 2, which depicts the Fourier transform analysis spectra of CSMA, PEI, and CSMA-PEI. The analytic technology was well known by the skilled person in this art, and its experimental method was not illustrated herein. In FIG. 2, the peaks of CSMA-PEI showed the characteristic bonding of CSMA and PEI, and the more significant part was primary amine of PEI (2846 cm$^{-1}$, 1948 cm$^{-1}$). CSMA originally only had amide peak while the peak of primary amine appeared post Michael addition with PEI, proving that CSMA-PEI gene carrier was successfully synthesized in the invention.

Figure 3:
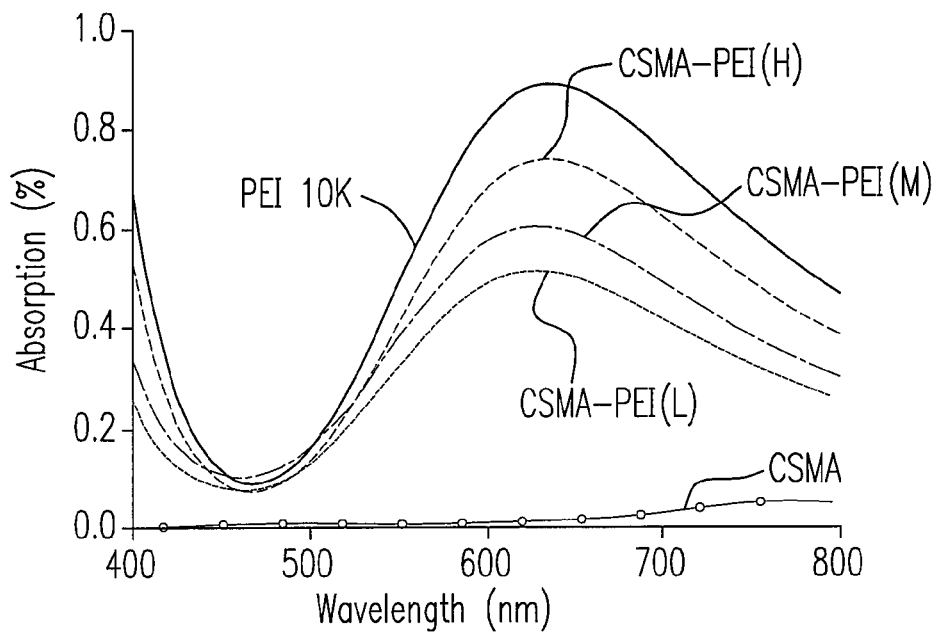
FIG. 3 depicts the UV/visible spectra of CSMA, PEI and CSMA-PEI.

In quantification, please refer to FIG. 3, which depicts the UV/visible spectra of CSMA, PEI, and CSMA-PEI. The spectrum analysis technology was well known by the skilled person in this art, and its experimental method was not illustrated herein. Since the lone-pair electrons of amino group of PEI and cupric bromide formed chelate, which had specific absorption at a wavelength of 630 nm, the amount of CSMA bound to PEI could be determined by using PEI standard curve. Since CSMA did not have specific absorption at 630 nm, it also could be known that covalent bonding was formed between CSMA and PEI.

Figure 4:
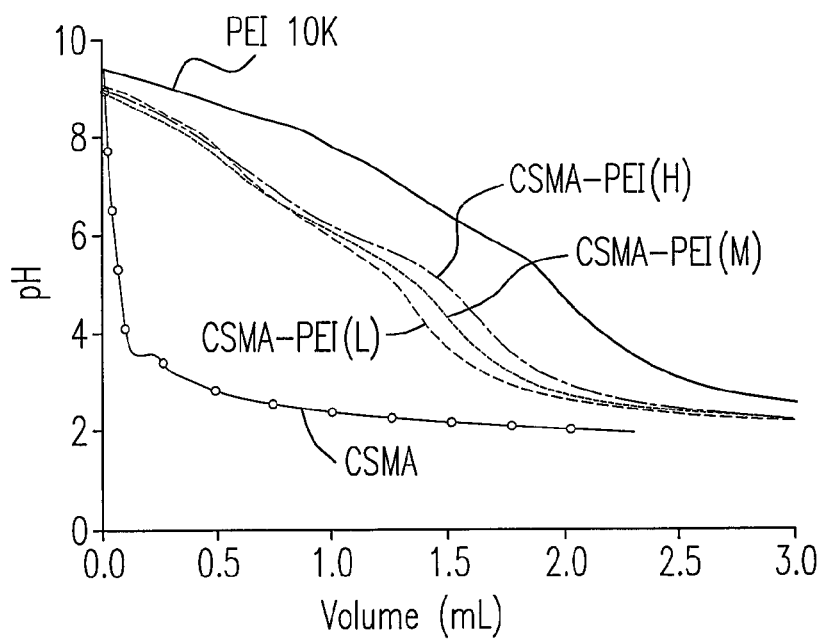
FIG. 4 depicts the buffering capability analytic spectrum of CSMA, PEI and CSMA-PEI.

As the properties of PEI disclosed in Paragraph [0003] of the invention, the buffering capacity which is very important to gene carrier would be determined in this experiment. Therefore, buffering capacity assay of CSMA-PEI gene carrier was also determined in the invention, and the aqueous solution (material concentration of 1 mg/mL) was titrated with 0.1 N HCl to observe the variation of pH value. As shown in FIG. 4, CSMA-PEI of the respective ratios could sustain the more constant pH value, indicating that CSMA-PEI of the invention still maintained the buffering efficiency in cells.

In particle size determination, please refer to Table 1, which shows that the diameter of CSMA-PEI/pEGFP-C1 nanoparticle was smaller than 185 nm after CSMA-PEI gene carrier with different amounts of PEI carried pEGFP-C1 plasmid DNA, and the size was gradually reduced with the increase in N/P ratio. From the surface potential analysis of CSMA-PEI/pEGPF-C1 nanoparticles, it would be known that nanoparticles of other N/P ratios carried positive charge except that surface potential was negative at N/P=1. It could also be known from TEM that CSMA-PEI/pEGPF-C1 nanoparticles showed as round shape (data not shown).

Figure 5A:
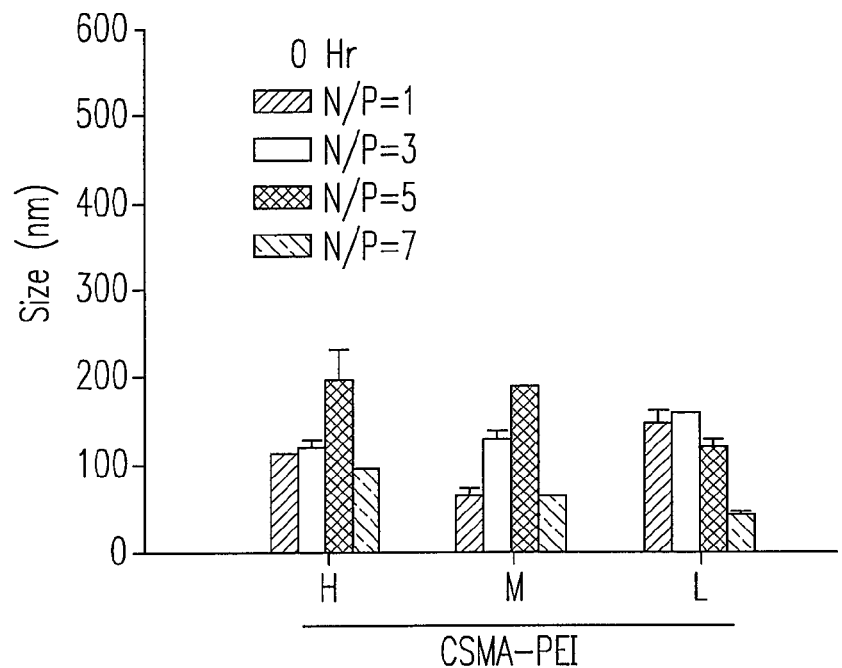
FIG. 5(a) to FIG. 5(c) respectively depicts the size comparison of CSMA-PEI/pEGFP-C1 nanoparticles which are stored in 10% FBS for (a) 0 hour, (b) 2 hours and (c) 4 hours after CSMA-PEI gene carriers with various amounts of PEI are mixed with pEGFP-C1 with different N/P ratios.
Figure 5B:
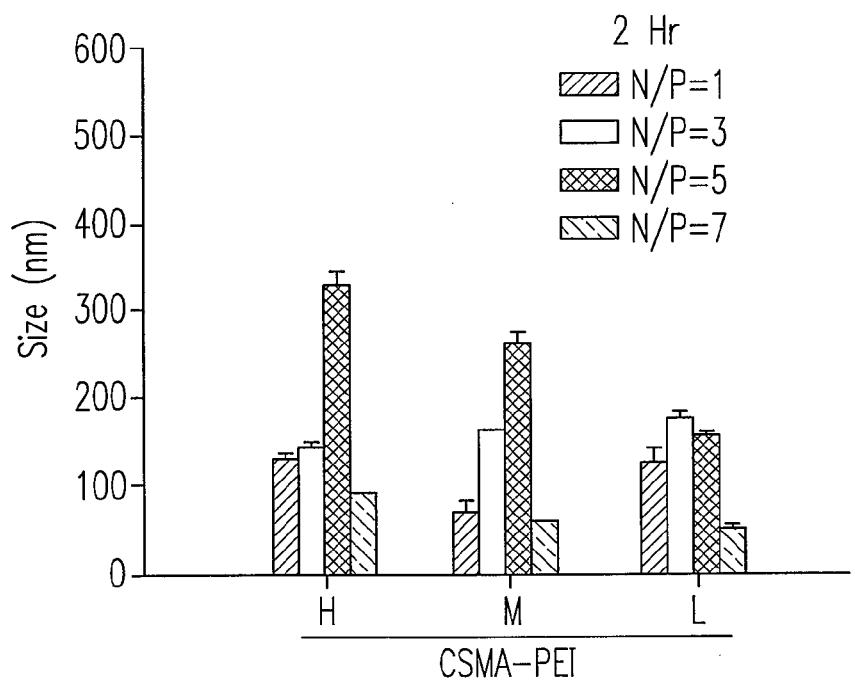
Figure 5C:
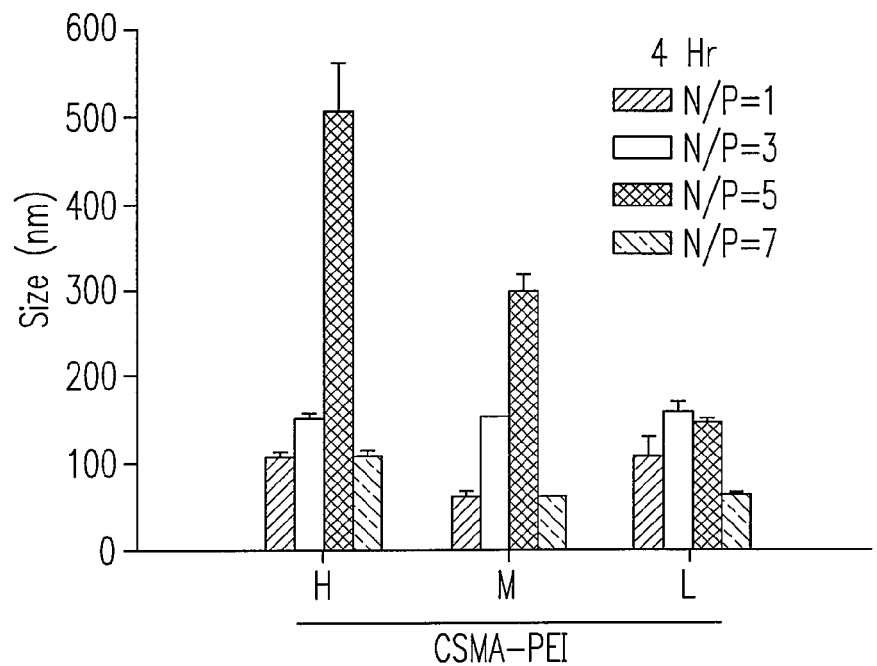

VII. Influence of Serum on CSMA-PEI/pEGPF-C1 Nanoparticles:

Please refer to FIGS. 5(a) to 5(c), the mixing of CSMA-PEI/pEGPF-C1 nanoparticles (based on the various N/P ratios) with 10% FBS would make nanoparticles influenced at different degrees subjected to serum, wherein N/P=7 had less influence and the diameter of nanoparticles sustained below 100 nm (compared with sizes in Table 1). As CSMA-PEI gene carriers with different amounts of PEI (i.e. CP(H), CP(M), and CP(L)), the size of CSMA-PEI/pEGPF-C1 nanoparticle formed by "CSMA-PEI" gene carrier and plasmid DNA had the lowest influence subjected to serum.

For understanding the protection ability of CSMA-PEI gene carrier of the invention on plasmid DNA, whether plasmid DNA was encapsulated by CSMA-PEI gene carrier was determined using agarose gel electrophoresis. Results showed that a partial of plasmid DNA still exposed from CSMA-PEI/pEGPF-C1 at N/P=1 while the results with respect to other N/P ratios showed that CSMA-PEI gene carrier completely encapsulated the plasmid DNA (data not shown). Additionally, CSMA-PEI/pEGPF-C1 nanoparticles was not influenced by serum under the condition of 10% FBS, and plasmid DNA was still exposed out at N/P=1 (data not shown), confirming that the gene carrier having polyelectrolyte structure in the invention had very high stability.

VIII. Efficiency of CSMA-PEI/pDNA Nanoparticles on Transfecting Genes:

In this experiment, the transfection efficiency of gene carrier carrying gene was evaluated by green fluorescence expression. Please refer to FIG. 6, it could be known that CSMA-PEI/pEGFP-C1 nanoparticles had high green fluorescence expression at high, middle and low PEI contents, and transfection increased with an increase in N/P ratio. The transfection effect of U87 cells was the best at N/P=7, and compared with "PEI", the transfection efficiency of the CSMA-PEI gene carriers with high, middle, or low PEI content which carried pEGFP-C1 increased.

Figure 6:
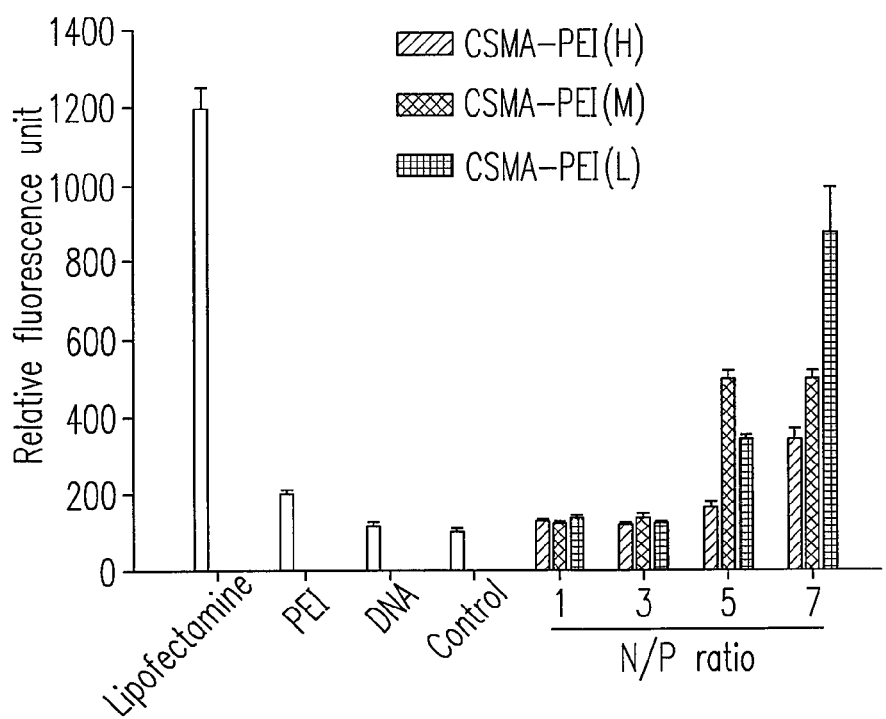
FIG. 6 depicts the fluorescence comparison of CSMA-PEI/pEGFP-C1 nanoparticles after transfection, wherein the nanoparticles are prepared with various amounts of PEI and different N/P ratios.

It could be known from FIG. 6 that pEGFP-C1 was delivered into U87 cells by CSMA-PEI gene carrier to abundantly express green fluorescence protein and cells were not died, indicating that high biocompatibility of CS leads to reducing

TABLE 1

DLS analysis of CSMA-PEI/pEGPF-C1 nanoparticles

|  | Intensity of scattered light (kcps) | Polydispersity index (PDI) | Size (nm) | Zeta potential (mV) |
| --- | --- | --- | --- | --- |
| CSMA-PEI/pEGFP-CP(H) | | | | |
| N/P = 1 | 104.17 ± 5.24 | 0.353 ± 0.040 | 182.47 ± 10.66 | −24.10 ± 0.99 |
| N/P = 3 | 154.75 ± 4.60 | 0.366 ± 0.092 | 167.90 ± 1.13 | 9.66 ± 0.33 |
| N/P = 5 | 143.65 ± 11.24 | 0.326 ± 0.004 | 119.50 ± 4.38 | 17.90 ± 2.69 |
| N/P = 7 | 136.25 ± 10.68 | 0.539 ± 0.122 | 76.25 ± 5.31 | 20.00 ± 2.40 |
| CSMA-PEI/pEGFP-CP(M) | | | | |
| N/P = 1 | 104.05 ± 9.83 | 0.355 ± 0.024 | 142.20 ± 14.28 | −23.30 ± 1.13 |
| N/P = 3 | 179.20 ± 60.81 | 0.235 ± 0.043 | 128.40 ± 16.26 | 2.16 ± 2.81 |
| N/P = 5 | 209.00 ± 12.73 | 0.306 ± 0.038 | 133.95 ± 0.21 | 15.90 ± 1.48 |
| N/P = 7 | 190.00 ± 2.40 | 0.562 ± 0.074 | 87.23 ± 9.27 | 15.60 ± 1.84 |
| CSMA-PEI/pEGFP-CP(L) | | | | |
| N/P = 1 | 94.05 ± 5.73 | 0.689 ± 0.118 | 127.85 ± 18.03 | −18.60 ± 0.21 |
| N/P = 3 | 170.60 ± 5.80 | 0.516 ± 0.065 | 120.90 ± 7.78 | 19.20 ± 0.14 |
| N/P = 5 | 167.80 ± 14.00 | 0.543 ± 0.236 | 85.99 ± 0.11 | 16.20 ± 0.42 |
| N/P = 7 | 134.80 ± 31.68 | 0.696 ± 0.076 | 68.83 ± 11.84 | 22.80 ± 3.25 | the toxicity of PEI and makes the transfection efficiency of CSMA-PEI gene carrier better than that of PEI.

Figure 7:
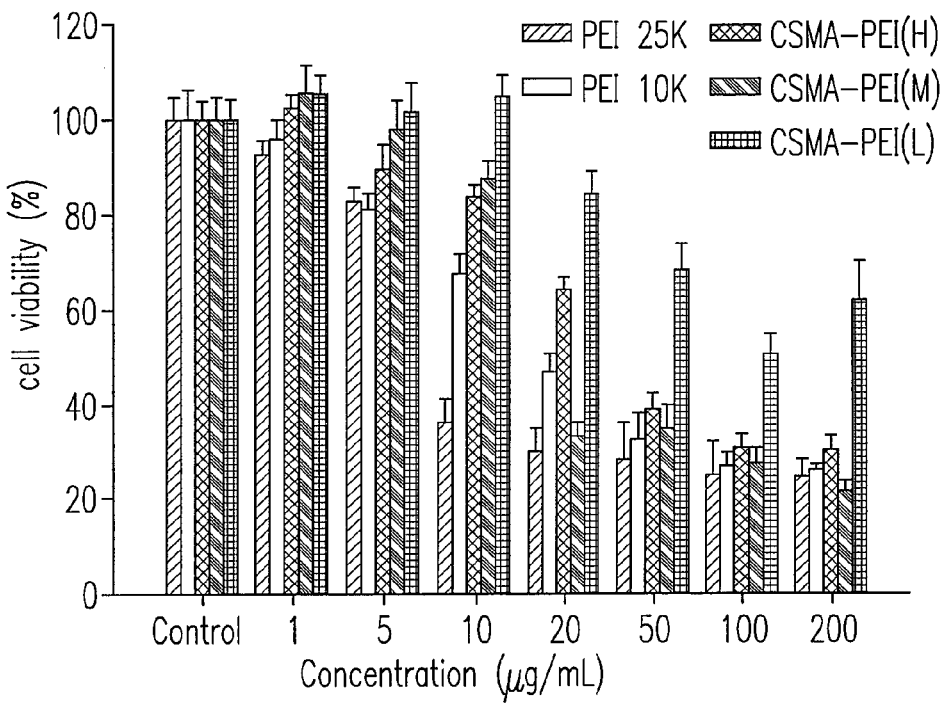
FIG. 7 depicts the cytotoxicity of the various concentrations of CSMA-PEI against U87 cells.
Figure 8:
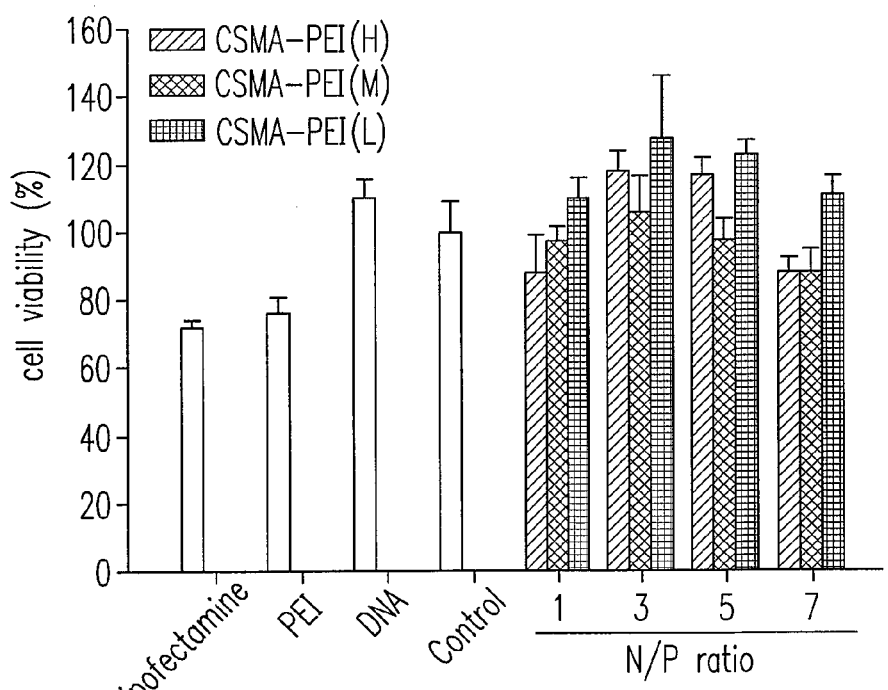
FIG. 8 depicts the cytotoxicity of CSMA-PEI/pEGFP-C1 nanoparticles transfected into U87 cells.

IX. Cytotoxicity of CSMA-PEI Gene Carrier and CSMA-PEI/pDNA Nanoparticles:

Please refer to FIG. 7, the cytotoxicity of the modified CSMA-PEI gene carrier was significantly reduced. CSMA-PEI gene carrier still sustained low toxicity compared with "PEI (control)" as a concentration of CSMA-PEI was 10 μg/mL, in particular in "CSMA-PEI (L)" group. When CSMA-PEI/pEGFP-C1 nanoparticles were made at various N/P ratios, the viability of U87 cells was up to more than 90% as compared with other controls, indicating that CSMA-PEI gene carrier and CSMA-PEI/pEGFP-C1 nanoparticles of the invention had low cytotoxicity (FIG. 8).

Figure 9:
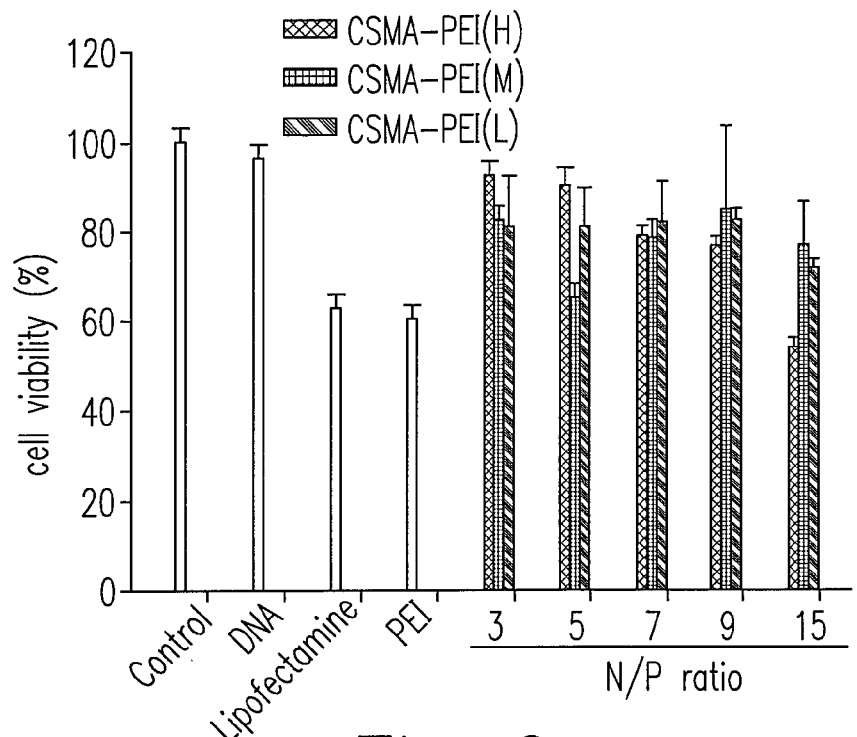
FIG. 9 depicts the cytotoxicity of CSMA-PEI/pGL3 nanoparticles transfected into U87 cells.
Figure 10:
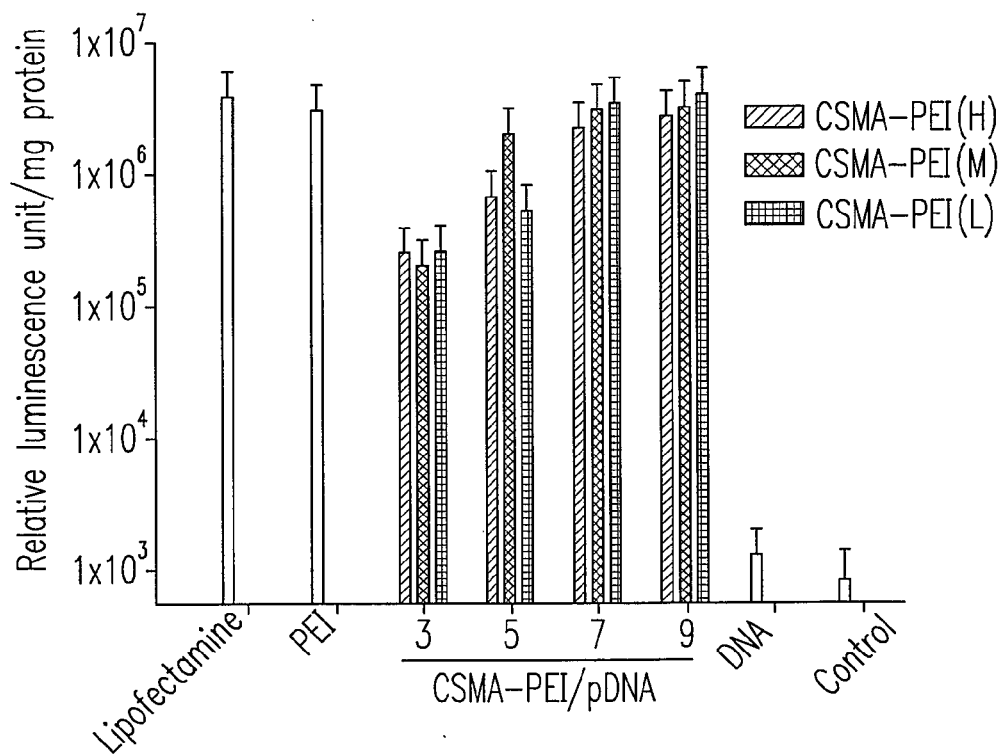
FIG. 10 depicts the relative luminescence intensity of CSMA-PEI/pGL3 nanoparticles transfected into U87 cells.

In addition to test the cytotoxicity of the gene carrier with the fluorescent pEGFP-C1, a luminescent plasmid pGL3 was also performed on cytotoxicity test of gene carrier with the pGL3. Please refer to FIG. 9, it was known that CSMA-PEI/pGL3 nanoparticles had the minimized cytotoxicity and compatible transfection efficiency (FIG. 10) as compared with control groups, "PEI/pGL3 at N/P=10" group and "Lipofectamine/pGL3" group. Thus, CSMA-PEI gene carrier was an adequate material to transport a genetic material into cells with the significantly reduced cytotoxicity (FIG. 8).

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A preparation method of a gene carrier, comprising steps of:
    reacting a chondroitin sulfate with a methacrylic anhydride to form a chondroitin sulfate-methacrylate; and
    covalently bonding a polyethylenimine with the chondroitin sulfate-methacrylate to form the gene carrier.

2. The preparation method according to claim 1 further comprising a step of precipitating the chondroitin sulfate-methacrylate with an ethanol.

3. The preparation method according to claim 1 further comprising a step of mixing the polyethylenimine with a pyridine.

4. The preparation method according to claim 1 further comprising a step of dialyzing the gene carrier to remove the redundant polyethylenimine.

5. The preparation method according to claim 4, wherein the dialyzing step is performed by using a dialysis membrane.

6. The preparation method according to claim 1 further comprising a step of mixing the gene carrier with a genetic material.

7. The preparation method according to claim 6, wherein the genetic material is selected from the group consisting of a DNA, an RNA, a complementary DNA, a micro RNA, and a small interfering RNA.

8. A gene carrier, comprising:
    a chondroitin sulfate;
    a methacrylic anhydride bonded with the chrondroitin chondroitin sulfate to form a chondroitin sulfate-methacrylate; and
    a polyethylenimine covalently bonded with a chondroitin sulfate-methacrylate to form the carrier.

9. The gene carrier according to claim 8, wherein the gene carrier is configured to carry a genetic material.

10. The gene carrier according to claim 9, wherein the genetic material is selected from the group consisting of a DNA, an RNA, a complementary DNA, a micro RNA, and a small interfering RNA.

11. A gene carrier, comprising:
    a negatively charged polysaccharide having a double-bond group; and
    a positively charged molecule having an amino group covalently bonded with the double-bond group.

12. The gene carrier according to claim 11, wherein the negatively charged polysaccharide is selected from a group consisting of a chondroitin sulfate, a heparin and a hyaluronic acid.

13. The gene carrier according to claim 11, wherein the double-bond group is originated from one of an acrylate and a methacrylate and is a carbon-carbon double-bond group selected from a group consisting of an acryloyl chloride, an acrylic anhydride, a methacryloyl chloride, and a methacrylic anhydride.

14. The gene carrier according to claim 11, wherein the positively charged molecule is one of a polyethylenimine and a polylysine.

* * * * *